(12) United States Patent
Botzer et al.

(10) Patent No.: US 11,642,146 B2
(45) Date of Patent: May 9, 2023

(54) FRENULUM SPREADER

(71) Applicant: Bam Medical Ltd., Tel Aviv (IL)

(72) Inventors: Eyal Botzer, Ramat Hasharon (IL); Or Agassi, Tel Aviv (IL); Reuven Marko, Netanya (IL); Avishay Keren, Mishmeret (IL)

(73) Assignee: BAM MEDICAL LTD., Tel Aviv (IL)

( * ) Notice: Subject to any disclaimer, the term of this patent is extended or adjusted under 35 U.S.C. 154(b) by 700 days.

(21) Appl. No.: 16/735,047

(22) Filed: Jan. 6, 2020

(65) Prior Publication Data
US 2020/0138461 A1 May 7, 2020

Related U.S. Application Data

(63) Continuation of application No. 15/131,628, filed on Apr. 18, 2016, now Pat. No. 10,524,813.

(60) Provisional application No. 62/149,605, filed on Apr. 19, 2015.

(51) Int. Cl.
*A61B 17/24* (2006.01)
*A61B 17/32* (2006.01)
*A61B 17/00* (2006.01)
*A61B 17/34* (2006.01)

(52) U.S. Cl.
CPC ............... *A61B 17/24* (2013.01); *A61B 17/32* (2013.01); *A61B 2017/00907* (2013.01); *A61B 2017/320044* (2013.01); *A61B 2017/345* (2013.01)

(58) Field of Classification Search
CPC ............ A61B 17/24; A61B 2017/0212; A61B 217/0225; A61B 217/0231; A61B 17/4241
See application file for complete search history.

(56) References Cited

U.S. PATENT DOCUMENTS

| | | | |
|---|---|---|---|
| 455,972 A | 7/1891 | Oudin et al. | |
| 1,879,609 A | 9/1932 | Mildred | |
| 2,129,496 A | 9/1938 | Alice | |
| 2,389,237 A | 11/1945 | Petrullo | |
| 2,437,812 A | 3/1948 | A | |
| 2,637,031 A | 5/1953 | Friedman | |
| 3,511,242 A * | 5/1970 | Agnone | A61B 17/0493 128/880 |
| 3,727,605 A | 4/1973 | Klein | |
| 4,251,897 A | 2/1981 | Alam | |
| 4,327,744 A | 5/1982 | Smith | |
| 4,415,550 A | 11/1983 | Pakhomov et al. | |

(Continued)

FOREIGN PATENT DOCUMENTS

CN 2044173 U 9/1989
WO 2015083146 A1 6/2015

OTHER PUBLICATIONS

The International Search Report and The Written Opinion for PCT/US2016/056283, ISA/RU, Moscow, Russia, dated Jan. 19, 2017.

*Primary Examiner* — David W Bates
(74) *Attorney, Agent, or Firm* — M&B IP Analysts, LLC

(57) ABSTRACT

An apparatus for spreading tissues. The apparatus includes a sheath member including an open end, a closed end, and a barrel extending between the open end and the closed end; and at least one flap-tip for engaging with tissues, wherein the at least one flap-tip is attached to the sheath member, each flap-tip projecting from the sheath member, wherein the at least one flap-tip is moved in response to movement of the sheath member.

10 Claims, 3 Drawing Sheets

(56) References Cited

U.S. PATENT DOCUMENTS

| | | | |
|---|---|---|---|
| 4,422,131 A * | 12/1983 | Clanton | F21V 23/0414 |
| | | | 362/186 |
| 4,694,843 A | 9/1987 | Casenhiser | |
| 4,718,662 A | 1/1988 | North | |
| 4,899,737 A | 2/1990 | Lazarian | |
| 5,095,897 A | 3/1992 | Clark et al. | |
| 5,112,227 A | 5/1992 | Bull | |
| 5,383,846 A | 1/1995 | Short | |
| 5,397,332 A | 3/1995 | Kammerer et al. | |
| 5,517,692 A | 5/1996 | Wunderlich-Kehm | |
| 5,535,105 A * | 7/1996 | Koenen | A61B 42/10 |
| | | | 362/570 |
| 5,554,076 A | 9/1996 | Clark | |
| 5,640,713 A | 6/1997 | Ping | |
| 5,643,232 A | 7/1997 | Villotti, Jr. | |
| 5,718,243 A | 2/1998 | Weatherford et al. | |
| 6,074,343 A | 6/2000 | Nathanson et al. | |
| 6,115,958 A | 9/2000 | Enderle | |
| 6,212,435 B1 | 4/2001 | Lattner et al. | |
| 6,422,243 B1 | 7/2002 | Daram | |
| 6,618,627 B2 | 9/2003 | Lattner et al. | |
| 6,711,746 B1 | 3/2004 | Orellana | |
| 6,772,465 B2 | 8/2004 | Mehta | |
| 6,851,430 B2 | 2/2005 | Tsou | |
| 6,896,681 B1 | 5/2005 | Watson | |
| 6,902,289 B1 | 6/2005 | Smith | |
| 7,214,336 B2 | 5/2007 | Sheridan et al. | |
| 7,346,955 B2 | 3/2008 | Laforcade | |
| D595,508 S * | 7/2009 | Wagner | D4/103 |
| D605,406 S * | 12/2009 | Wagner | A61C 17/00 |
| | | | D4/103 |
| D617,563 S * | 6/2010 | Wagner | D4/105 |
| 7,744,137 B2 | 6/2010 | Mazyek | |
| 8,356,598 B2 | 1/2013 | Rumsey | |
| 8,425,412 B2 | 4/2013 | Rucker | |
| 8,740,788 B1 * | 6/2014 | Mettler, Jr. | A61B 17/244 |
| | | | 600/240 |
| 8,915,848 B1 | 12/2014 | Rixen | |
| D756,658 S | 5/2016 | Capozza et al. | |
| 2002/0173701 A1 | 11/2002 | Kolata et al. | |
| 2003/0060685 A1 * | 3/2003 | Houser | A61B 17/0218 |
| | | | 600/206 |
| 2004/0193211 A1 | 9/2004 | Voegele et al. | |
| 2006/0166161 A1 | 7/2006 | Rose et al. | |
| 2008/0071208 A1 | 3/2008 | Voegele et al. | |
| 2008/0172000 A1 * | 7/2008 | Perez | A61B 17/12 |
| | | | 604/198 |
| 2008/0243174 A1 | 10/2008 | Oren et al. | |
| 2009/0227846 A1 | 9/2009 | Beck | |
| 2010/0042229 A1 | 2/2010 | Hawk | |
| 2010/0147315 A1 | 6/2010 | Chodorow | |
| 2010/0204640 A1 | 8/2010 | Mingozzi et al. | |
| 2010/0211150 A1 | 8/2010 | Arx | |
| 2010/0319149 A1 | 12/2010 | Phillips | |
| 2015/0057501 A1 | 2/2015 | Livne et al. | |
| 2015/0265267 A1 * | 9/2015 | Tran | A61B 17/24 |
| | | | 700/119 |
| 2016/0045020 A1 | 2/2016 | Belge-Barnes | |

* cited by examiner

FRENULUM SPREADER

CROSS-REFERENCE TO RELATED APPLICATIONS

This application is a continuation of U.S. patent application Ser. No. 15/131,628, filed on Apr. 18, 2016, now allowed which claims the benefit of U.S. Provisional Application No. 62/149,605 filed on Apr. 19, 2015, the contents of which are hereby incorporated by reference.

TECHNICAL FIELD

The present disclosure relates generally to devices for spreading oral tissue, and more specifically to devices for preventing reattachment of tissue after procedures.

BACKGROUND

A frenulum is a typically small fold of tissue that secures or restricts motion of a mobile organ. Several frenula exist in the human mouth, such as the lingual frenulum under the tongue, the frenulum labii superioris inside the upper lip, the frenulum labii inferioris inside the lower lip, and the buccal frena which connect the cheeks to the gum. A lingual frenulum is a fold of mucous membrane extending from the floor of the mouth to the midline of the underside of the tongue. The lingual frenulum is formed during normal embryonic development and undergoes apoptosis as the tongue develops, thereby retracting away from the tip of the tongue and increasing the tongue's mobility.

Disturbances in embryonic oral development may result in Ankyloglossia (also known as "tongue tie"), a congenital oral anomaly in which a lingual frenulum connects the midline of the tongue underside with the floor of the mouth. Ankyloglossia varies in degree of severity, from mild cases characterized by mucous membrane bands to complete Ankyloglossia, in which the tongue, attached to a lingual frenulum, is tethered to the floor of the mouth.

Ankyloglossia in infants is associated with difficulties in breastfeeding such as failure to thrive, maternal nipple damage, maternal breast pain, poor milk supply, breast engorgement, and refusing the breast. Infants with restrictive Ankyloglossia may not be able to extend their tongues over the lower gum line to form a proper seal and must use their jaws to keep the breast in the mouth. Ankyloglossia in infants can lead to a range of problems, such as difficulties breastfeeding, speech impediments, poor oral hygiene, and social problems during childhood and adolescence.

The most common treatment for Ankyloglossia is a surgical procedure termed Frenulotomy, also commonly known as Frenotomy. During this procedure, an incision is made several millimeters into the lingual frenulum. The procedure is typically brief, and is usually accompanied by minimal bleeding and discomfort. The procedure is typically made using surgical scissors, a scalpel, a laser source, and/or other surgical tools. Complications of frenotomy may include infection, hemorrhaging caused by severance of the lingual artery, and asphyxia caused by the released tongue falling back into the airway.

Following frenotomy in infants, it is recommended that the parent or other caregiver help the infant perform exercises to elevate the infant's tongue and/or to expend a patient's lip (depending on the type of frenotomy performed). These exercises are considered to be important for preventing the recurrence of tongue frenulum formation and for inducing tongue muscle function.

Current literature suggests post-frenotomy use of "active wound management," i.e., the stretching of tethered oral tissues in a patient's mouth to prevent the reattachment of a frenulum by using two fingers to be placed beside the patient's frenulum and repeatedly stretching the frenulum. The active wound management exercises are typically performed by inserting a finger, a tongue blade, or a cotton swab into the infant's mouth and manually lifting the tongue. However, such exercises are often accompanied by discomfort for the infant and psychological distress for the administering caregiver. In particular, parents or other individuals performing the active wound management exercises may find the exercises difficult to handle effectively, especially in newborns when the mouth is small and delicate.

It would therefore be advantageous to provide a solution that would overcome the deficiencies of the prior art.

SUMMARY

A summary of several example embodiments of the disclosure follows. This summary is provided for the convenience of the reader to provide a basic understanding of such embodiments and does not wholly define the breadth of the disclosure. This summary is not an extensive overview of all contemplated embodiments, and is intended to neither identify key or critical elements of all embodiments nor to delineate the scope of any or all aspects. Its sole purpose is to present some concepts of one or more embodiments in a simplified form as a prelude to the more detailed description that is presented later. For convenience, the term "some embodiments" may be used herein to refer to a single embodiment or multiple embodiments of the disclosure.

Certain embodiments disclosed herein relate to an apparatus for spreading tissues.

The apparatus comprises a sheath member including an open end, a closed end, and a barrel extending between the open end and the closed end; and at least one flap-tip for engaging with tissues, wherein the at least one flap-tip is attached to the sheath member, each flap-tip projecting from the sheath member, wherein the at least one flap-tip is moved in response to movement of the sheath member.

Certain embodiments disclosed herein also relate to another apparatus for spreading tissues. The apparatus comprises a tubular member including a first open and, a second open end, and a barrel extending between the first open end and the second open end; and at least one flap-tip for engaging with tissues, wherein the at least one flap-tip is attached to the tubular member, each flap-tip projecting from the tubular member, wherein the at least one flap-tip is moved in response to movement of the tubular member.

BRIEF DESCRIPTION OF THE DRAWINGS

The subject matter disclosed herein is particularly pointed out and distinctly claimed in the claims at the conclusion of the specification. The foregoing and other objects, features, and advantages of the disclosed embodiments will be apparent from the following detailed description taken in conjunction with the accompanying drawings.

DETAILED DESCRIPTION

Figure 1:
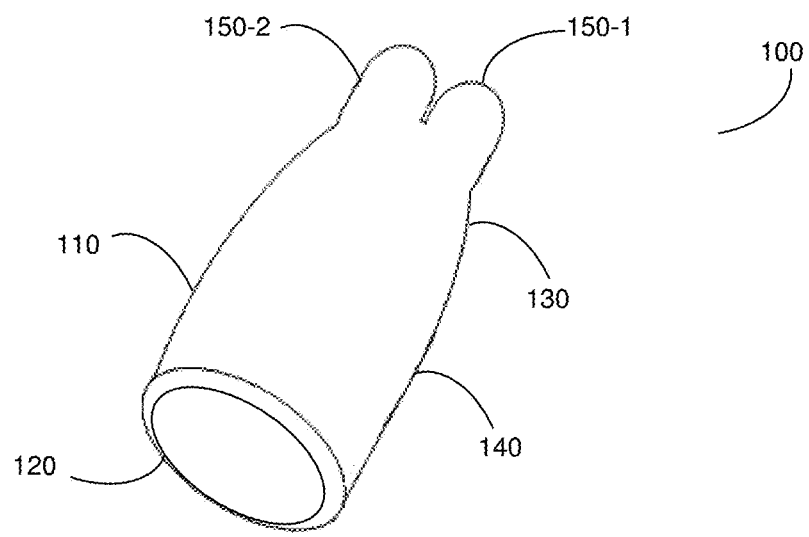
FIG. 1 is a schematic diagram of a sheath member according to an embodiment.

It is important to note that the embodiments disclosed herein are only examples of the many advantageous uses of the innovative teachings herein. In general, statements made in the specification of the present application do not necessarily limit any of the various claimed embodiments. Moreover, some statements may apply to some inventive features but not to others. In general, unless otherwise indicated, singular elements may be in plural and vice versa with no loss of generality. In the drawings, like numerals refer to like parts through several views.

The various disclosed embodiments include an apparatus for spreading oral tissues and for further preventing reattachment of tissue after a separation procedure. In particular, the disclosed embodiments may be utilized to spread a frenulum. Furthermore, the disclosed embodiments may be utilized to spread a frenulum following a Frenotomy procedure. In an embodiment, the apparatus includes a sheath member including an open end, a closed end, and a barrel extending between the open end and the closed end; and one or more flap-tip members projecting from the sheath member.

FIG. 1 shows an example left view schematic diagram 100 of a sheath member 110 according to an embodiment. In the example embodiment shown in FIG. 1, the right side view (not shown) of the sheath member is identical to the left side view. In an embodiment, the sheath member 110 is made of a bio-compatible material such that it can safely be inserted into at least a human mouth.

The sheath member 110 includes an open end 120, a closed end 130, and a barrel 140 extending between the open end 120 and the closed end 130. In an embodiment, the open end 120 is designed to fit over a caregiver's hand or portions thereof (in particular, one or more fingers), thereby allowing insertion of such hand or portion thereof into the barrel 140 in order to spread one or more frenula. In particular, the sheath member 110 may be designed to spread oral frenula. Such spreading using the sheath member 110 may be utilized to, for example, exercise a frenulum after a frenotomy, thereby hindering reattachment of the frenulum. Such exercise may further be used for spreading the frenulum in order to flex a patient's tongue and increase its movement. In the embodiment shown in FIG. 1, the barrel 140 is a roughly cylindrical component in which portions of a caregiver's hands may be inserted.

The sheath member 110 further includes one or more flap-tips 150 affixed to the closed end 130 and/or to the barrel 140. In the embodiment shown in FIG. 1, the sheath member 110 includes flap-tips 150-1 and 150-2 (hereinafter referred to individually as a flap-tip 150 and collectively as flap-tips 150, merely for simplicity purposes) attached to the closed end 130 and projecting freely therefrom. Each flap-tip 150 may be attached, affixed, joined, or otherwise connected to the closed end 130 at a bottom end of the flap-tip 150.

In an embodiment, the flap-tips 150 are at least partially flat in shape, thereby allowing for easier insertion into a patient's mouth and/or easier operation during exercises. The flap-tips 150 may further be flexible, thereby allowing a caregiver to move the flap-tips 150 by inserting one or more fingers or portions thereof into the barrel 140 and moving the inserted finger(s).

The flap-tips 150 may be placed beside the frenulum in a frenotomy patient's mouth, thereby enabling a caregiver to manually lift the tongue, spread the upper lip, and/or any similar exercises or movements of tissue. As an example, a caregiver may insert his or her fingers in the sheath member 110 through the open end 120. The caregiver may further insert one of his or her fingers near the bottoms of the flap-tips 150 via the barrel 140 and/or the closed end 130. Thereafter, the caregiver may place the flap-tips 150 into a patient's mouth, typically beneath the patient's tongue, thereby allowing spreading of the frenulum by moving his or her fingers. Specifically, movement of the caregiver's finger(s) within the barrel 140 and/or against the closed end 130 may cause at least a portion of the sheath member 210 (e.g., the barrel 140 and/or the closed end 130) to flex, bend, or move, thereby causing movement of the flap-tips 150 projecting therefrom. The spreading and/or practicing of the frenulum increases the motion of the tongue and/or the lip. Such activity, after a frenotomy procedure, decreases the likelihood of reattachment of the frenulum. Furthermore, such activity may prevent the need for an initial or subsequent surgical procedure if made on a daily basis as the movement range of the frenulum is likely to increase.

In another embodiment, the flap-tip 150 and/or the closed end 130 may be detachable and, thus, may be replaced after use. Such replacement allows for ensuring sterile operations while using the sheath member 110 and/or for using different flap-tips (e.g., made of different materials, in different shapes, having different sizes, and so on) during different exercise sessions.

Figure 2:
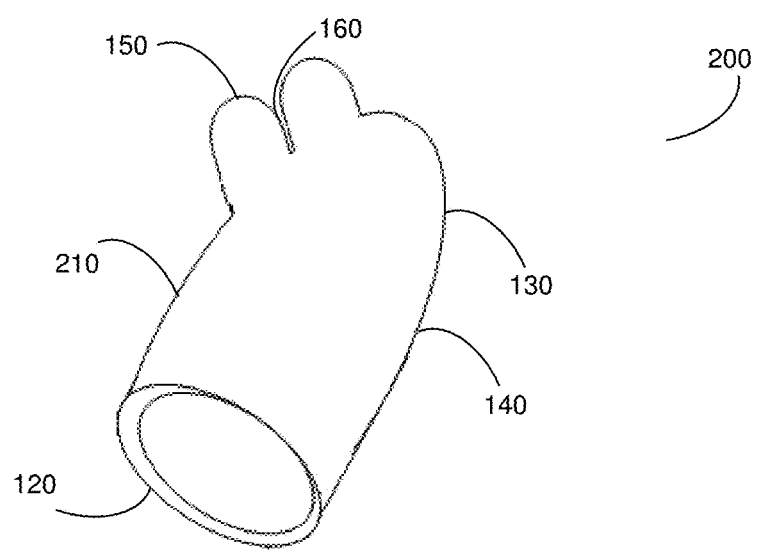
FIG. 2 is a schematic diagram of a sheath member according to another embodiment.

FIG. 2 is an example schematic diagram 200 of a side view of a sheath member 210 according to another embodiment. The sheath member 210 includes an open end 120, a closed end 130, and a barrel 140 extending between the open end 120 and the closed end 130. The sheath member 210 includes a single flap-tip 150 that is partially split at a length 160 along the flap-tip 150. In the example embodiment shown in FIG. 2, the flap-tip 150 is attached to the barrel 140. In particular, in FIG. 2, the flap-tip 150 is attached to a portion of the barrel 140 near the closed end 130. The flap-tip 150 may be attached, affixed, joined, or otherwise connected to the barrel 140 at a bottom end of the flap-tip 150 and projecting freely therefrom.

In an embodiment, at least part of the sheath member 210 is coated with a biocompatible material. In a further embodiment, the biocompatible material may have soft tactile properties. The biocompatible material may be, but is not limited to, natural rubber, silicone, polyvinylchloride (PVC), phthalate-free PVC, latex, nylon, polyethersulfone, acrylonitrile butadiene styrene, polypropylene, polycarbonate, a Kraton polymer, a combination thereof, and the like.

In an embodiment, a light source (not shown) may be integrated in, for example, the closed end 130. The light source may be, but is not limited to, a light-emitting diode (LED). The light source may be directed so as to cast light on the environment around the sheath member 210. In another embodiment, the sheath member 210 may be made of transparent material. Such transparent material may allow a light source to be integrated within the sheath member 210 and to illuminate the sheath member 210.

As a non-limiting use example, a caregiver may insert one or more fingers into the barrel 140 of the sheath member 210 via the open end 120. Thereafter, the caregiver may move the inserted fingers within the barrel 140 to cause movement of the flap-tip 150. In particular, the finger movement may cause portions of the barrel to flex, bend, or otherwise move, thereby causing the flap-tips 150 projecting therefrom to be moved accordingly. If a light source is integrated in the closed end 130, light may be projected into, e.g., a patient's mouth when the closed member 130 is placed therein. The illumination may help guide the caregiver to the portion of the mouth to be exercised. If a light source is integrated in the sheath member 210 and the sheath member 210 is transparent, the sheath member 210 may be illuminated, thereby allowing the caregiver to see both the sheath member 210 and one or more portions of the patient's mouth more easily.

Figure 3:
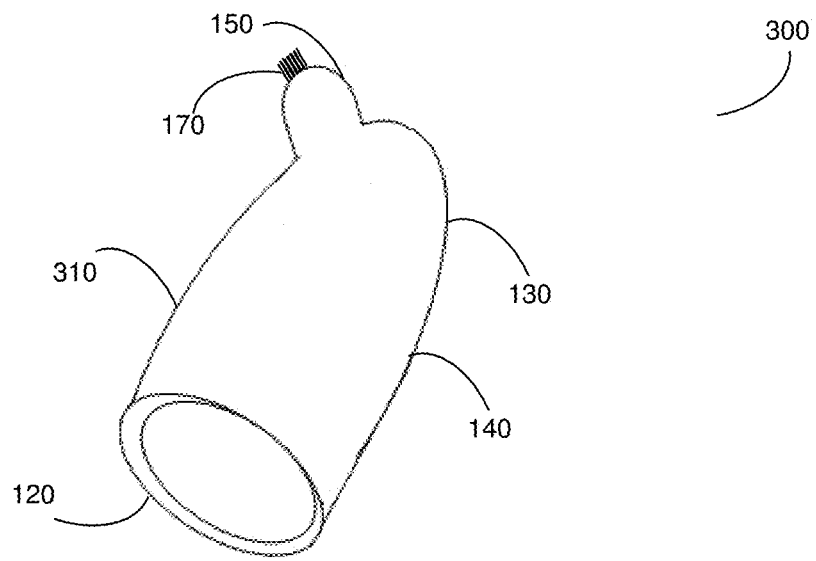
FIG. 3 is a schematic diagram of a sheath member according to yet another embodiment.

FIG. 3 is an example schematic diagram 300 illustrating a side view of a sheath member 310 according to yet another embodiment. The sheath member 310 includes an open end 120, a closed end 130, and a barrel 140 extending between the open end 120 and the closed end 130. In the embodiment shown in FIG. 3, the sheath member 310 includes only one flap-tip 150 for, e.g., stretching a patient's frenulum.

In an embodiment, the sheath member 310 further includes a plurality of tines 170 disposed on and projecting from at least a portion of the flap-tip 150. In the example embodiment shown in FIG. 3, the tines are disposed on and projecting freely from a top end of the flap-tip 150. Thus, when the caregiver utilizes the sheath member 310 and moves the flap-tip 150, the tines 170 come into contact with various portions of the patient's body (e.g., tissues in the mouth).

The tines 170 may be made of, e.g., a carrier material. The carrier material may include a healing material for cleaning and/or otherwise promoting healing such as, but not limited to, an antibacterial substance, a sanitizing substance, a disinfectant substance (e.g., mouthwash), and the like. In a further embodiment, the tines 170 include an anesthetic material that may be released responsive to epidermal contact. The anesthetic material may be, but is not limited to, lidocaine, vapocoolants, eutectic mixtures of local anesthetics, formulations thereof, and the like.

Figure 4:
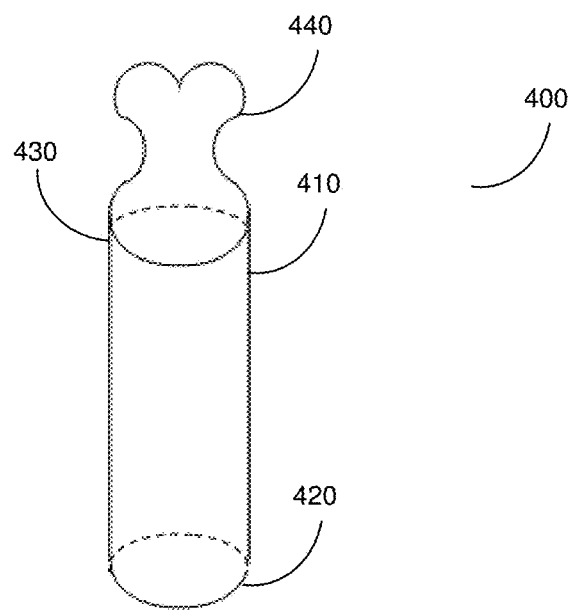
FIG. 4 is a schematic diagram of a tubular member according to an embodiment.

FIG. 4 is an example schematic diagram 400 of a tubular member 410 according to an embodiment. The tubular member 410 includes a first end 420 and a second end 430. A caregiver may insert one or more fingers through the first end 420 into the tubular member 410, and may stretch a patient's frenulum using a flap-tip 440 attached, affixed, joined, or otherwise connected to the second end 430. In the example embodiment shown in FIG. 4, the flap-tip 440 is split such that a patient's frenulum may be laid thereon.

In another embodiment, the flap-tip 440 may have a two-ear shape such that a patient's frenulum can be laid there between. The tubular member 410 is typically made at least in part of a flexible material to allow a caregiver to move the tubular member 410 and/or any portion thereof.

Figure 5:
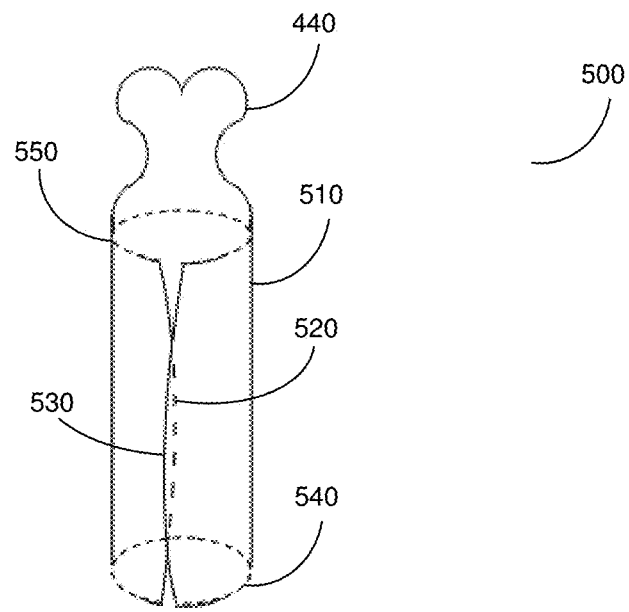
FIG. 5 is a schematic diagram of a tubular member according to another embodiment.

FIG. 5 is an example schematic diagram 500 of a tubular member 510 according to another embodiment. The tubular member 510 includes a flap-tip 440 for frenulum spreading or similar exercises. The tubular member 510 is a sheet which is curved, molded, or otherwise shaped into a tubular shape, with a first longitudinal edge 520 and a second longitudinal edge 530 shaped so as to enable at least partial overlap between the longitudinal edges 520 and 530. When, for example, a finger is inserted from the bottom opening 540 toward the upper opening 550, the longitudinal edges 520 and 530 may separate from a first overlapping position to a second overlapping position, and may be further separated to a non-overlapping position as may be necessary to accommodate insertion of the fingers. The flap-tip 440 may be attached to, affixed to, or molded, formed, or otherwise created as a single component with the tubular member 510 as described further herein above with respect to FIG. 4.

Figure 6:
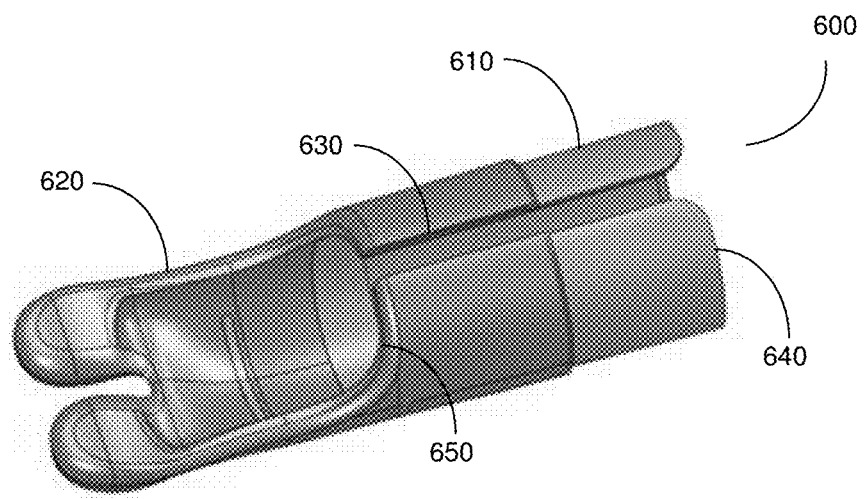
FIG. 6 is a schematic diagram of a tubular member according to another embodiment.

FIG. 6 is an example schematic diagram 600 of a tubular member 610 according to another embodiment. The tubular member 610 includes a flap-tip 620 for frenulum spreading or similar exercises projecting therefrom. In an embodiment, the tubular member 610 may be a sheet which is curved, molded, or otherwise shaped into a tubular shape having a longitudinal spread 630 extending between a bottom opening 640 and an upper opening 650. The longitudinal spread 630 enables the insertion of fingers in different sizes from the bottom opening 640 toward the upper opening 650. The flap-tip 620 may be attached to, affixed to, or molded, formed, or otherwise created as a single component with the tubular member 610 as described further herein above with respect to FIG. 4.

It should be noted that the embodiments described herein above are discussed with respect to a caregiver, a patient, and an oral frenulum merely for simplicity purposes and without limitation on the disclosed embodiments. The embodiments described may be utilized by any person seeking to stretch or otherwise exercise and/or spread tissue or other materials without departing from the scope of the disclosure. It should be further noted that the Ankyloglossia correction procedure, also commonly known as Frenotomy, may be executed using the apparatus as described herein above.

It should be further noted that components of the embodiments described herein above may be made of the same material or made of different materials. For example, the closed end 130 and/or flap-tip 150 may be made of natural rubber, while the open end 120 may be made of silicone. Additionally, different portions of a component may be made of different materials. For example, an outer portion of the open end 120 may be made of a biocompatible material, while an inner portion of the open end 120 may be made of a non-biocompatible material or a different biocompatible material.

It should further be noted that portions of the embodiments described herein above may be molded together or otherwise created as a single part, or may be created as separate parts and affixed. Any or all of the components may be made of flexible material to allow for ready operation by, e.g., a caregiver.

All examples and conditional language recited herein are intended for pedagogical purposes to aid the reader in understanding the principles of the disclosed embodiment and the concepts contributed by the inventor to furthering the art, and are to be construed as being without limitation to such specifically recited examples and conditions. Moreover, all statements herein reciting principles, aspects, and embodiments of the disclosed embodiments, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

What is claimed is:

1. An oral frenulum spreader, comprising:
   a flap-tip having a distal end and an opposite proximal end, the distal end of the flap-tip having a slit therein separating the flat-tip into a left portion and a right portion, wherein the left portion of the flap-tip and the right portion of the flap-tip are essentially coplanar, wherein the slit flap-tip is adapted to fit about the oral frenulum, and wherein the flap-tip is further adapted to allow for motion of the oral frenulum spreader about the oral frenulum, wherein the flap-tip further comprises a plurality of tines, wherein the plurality of tines are made from at least a carrier material, wherein the carrier material includes an anesthetic material, wherein the anesthetic material releases in response to epidermal contact.

2. The oral frenulum spreader of claim 1, wherein the flap-tip is further adapted to fit beneath a patient's tongue.

3. The oral frenulum spreader of claim 1, further comprising:
   a sheath member connected to the proximal end of the flap-tip.

4. The oral frenulum spreader of claim 3, wherein the sheath member is essentially tubular.

5. The oral frenulum spreader of claim 4, wherein the tubular sheath member if is further adapted to fit about a caregiver finger.

6. The oral frenulum spreader of claim 3, wherein the sheath member further comprising:
   a light source disposed within the sheath member.

7. The oral frenulum spreader of claim 3, wherein the at least one flap-tip is adapted to be detachable from the sheath member.

8. The oral frenulum spreader of claim 1, wherein the flap-tip is further adapted to stretch the patient's frenulum.

9. The oral frenulum spreader of claim 1, wherein the flap-tip is further adapted to spread the patient's frenulum.

10. The oral frenulum spreader of claim 1, wherein the left portion of the flap-tip and the right portion of the flap-tip are symmetrical.

\* \* \* \* \*